United States Patent [19]
Hutchins, IV

[11] 3,937,214
[45] Feb. 10, 1976

[54] ELECTROMEDICAL PATIENT MONITORING SYSTEM

[76] Inventor: Thomas B. Hutchins, IV, 310 Brynwood Lane, Portland, Oreg. 97229

[22] Filed: July 7, 1972

[21] Appl. No.: 269,747

[52] U.S. Cl............................................ 128/2.1 A
[51] Int. Cl.² ........................................ A61B 5/04
[58] Field of Search..... 128/2.05 D, 2.05 E, 2.05 G, 128/2.05 P, 2.05 R, 2.06 R, 2.1 P, 2.1 A, 2.1 R, 2 L, 2 P, 2 R

[56] References Cited
UNITED STATES PATENTS

| | | | |
|---|---|---|---|
| 2,634,721 | 4/1953 | Greenweed, Jr. | 128/2.05 E |
| 2,640,389 | 6/1953 | Liston | 128/2 L |
| 3,218,638 | 11/1965 | Honig | 128/2.1 R |
| 3,576,554 | 4/1971 | Temps, Jr. et al. | 128/2.1 A |
| 3,690,313 | 9/1972 | Weppner et al. | 128/2.1 P |

FOREIGN PATENTS OR APPLICATIONS

| | | | |
|---|---|---|---|
| 975,373 | 11/1964 | United Kingdom | 128/2.06 R |

*Primary Examiner*—William E. Kamm
*Attorney, Agent, or Firm*—Kolisch, Hartwell, Dickinson & Stuart

[57] ABSTRACT

An electromedical patient monitoring system having a minimum likelihood of electrical injury to a patient is provided. Signals from a body-contacting sensor are amplified and processed by self-contained, battery powered apparatus for display by an electrical monitor, such as a recorder. In a preferred embodiment, the apparatus includes an input circuit operatively connected to the sensor and including an AC amplifier. The output of the amplifier is inductively coupled to a synchronous detector, part of an output circuit operatively connected to the monitor. Operating power for both the amplifier and detector is derived from a battery-powered audio oscillator to which the input and output circuits are inductively coupled. Thus, the apparatus provides DC isolation of the sensor from both the monitor and from the power source for the apparatus. In addition, the apparatus includes provision for inductively coupling a portion of the oscillator output to an excitor circuit for a sensor of a type requiring excitation by electrical oscillations.

2 Claims, 2 Drawing Figures

U.S. Patent Feb. 10, 1976 3,937,214
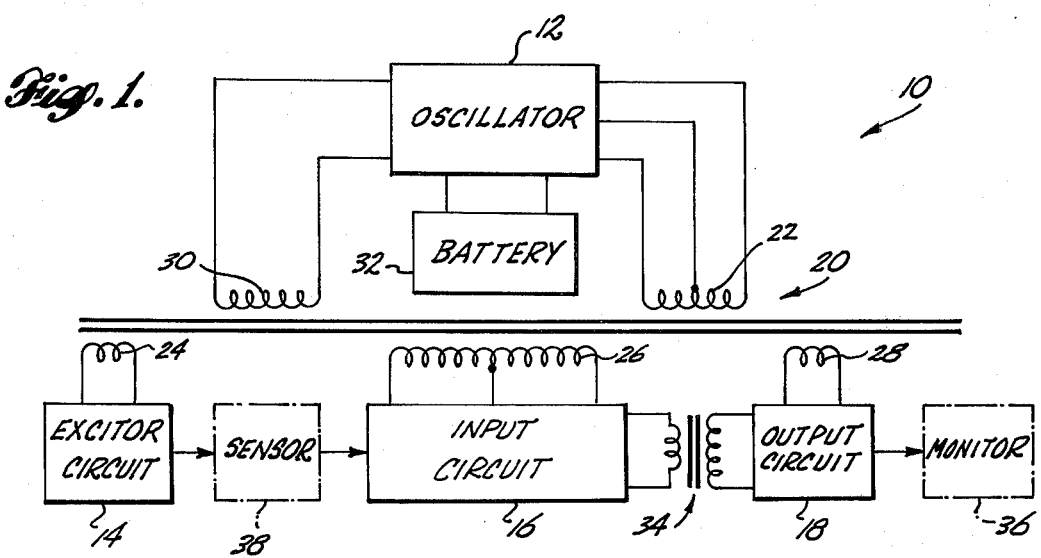
Fig. 1.
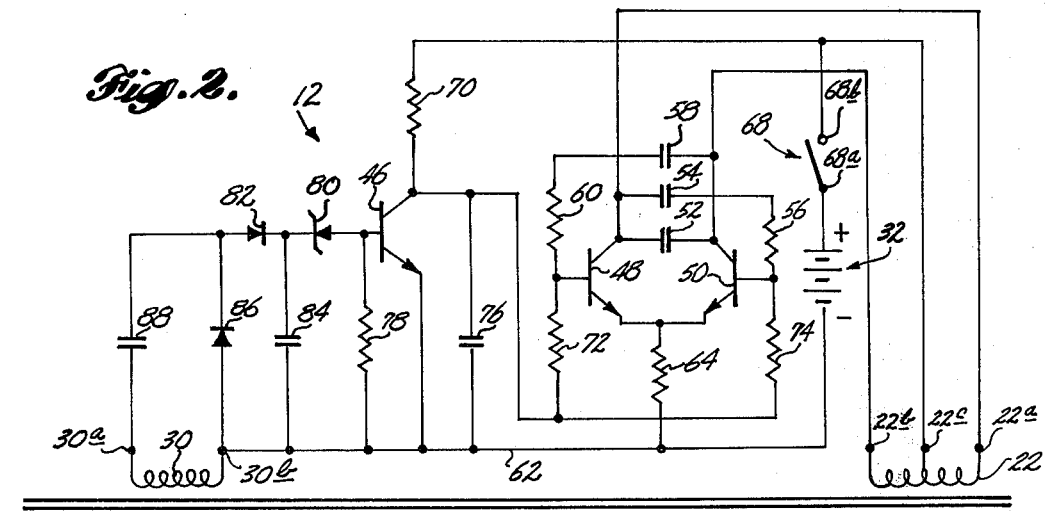
Fig. 2.
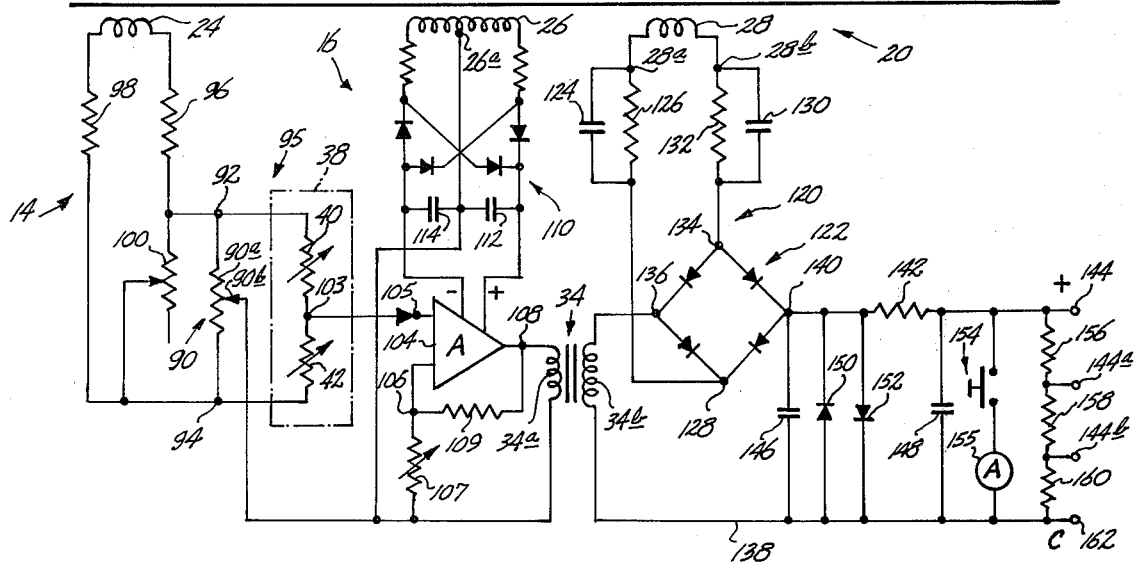

ELECTROMEDICAL PATIENT MONITORING SYSTEM

BACKGROUND AND SUMMARY OF THE INVENTION

The present invention relates to an electromedical patient-monitoring system. More particularly, it relates to a system whereby body-condition-related information, provided by a body-contacting sensor, is amplified and processed for display or recording by an electrical monitor with minimum electrical hazard to a patient.

During recent years, the use of electromedical patient-monitoring systems has become widespread. A system such as may be used in an intensive care facility typically consists of several electrical sensors for providing information on heart rate, blood pressure, etc. The output from these sensors is amplified or otherwise processed, and transmitted to a monitoring device which may display or record the information, and may sound an alarm if a monitored signal is outside preset limits. Such monitoring devices, because of their power requirements, ordinarily are powered by 50 or 60 Hz AC line current. Intermediate amplifiers or signal processors may be either battery or line current operated. Since the sensors are normally in direct contact with a patient's body, it is obviously quite important to minimize the possibility of harm to the patient from electrical devices connected to the sensor.

Accordingly, it is a general object of the invention to provide a patient monitoring system having a minimum likelihood of electrical injury to a patient. More specifically, it is an object to provide a system whereby harmful electrical potentials are prevented from being transmitted to a patient through body-contacting sensors.

A further object of the invention is to provide self-contained apparatus for receiving, processing, and transmitting sensor-derived body-condition-related information to an electrical monitor, which apparatus provides electrical isolation of a sensor from the monitor, from induced alternating current at power line frequencies, and from the power source for the apparatus itself.

According to a preferred embodiment of the invention, such a system includes an electromedical sensor of a type requiring electrical excitation. The needed excitation is supplied by coupling a portion of the output from a battery-powered oscillator to this sensor. A second portion of the oscillator output is used to power an amplifier which receives body-condition-related information from the sensor. A third portion of the oscillator output serves to synchronize a detector in an output circuit which processes the amplified information for display or recording by a monitor.

BRIEF DESCRIPTION OF THE DRAWINGS

These and other objects and advantages attained by the invention will become more apparent as the description which follows is read in conjunction with the accompanying drawings, wherein:

FIG. 1 is a block diagram illustrating a patient monitoring system according to the invention;

FIG. 2 is a schematic diagram illustrating electrical circuits employed in the system of FIG. 1.

DETAILED DESCRIPTION OF THE INVENTION

Turning now to the drawings, and referring first to FIG. 1, indicated generally at 10 is a patient-monitoring system according to the invention. Included in this system are an energizing circuit comprising constant amplitude audio oscillator 12, an excitor circuit 14, an input circuit 16, and an output circuit 18. A first inductive coupling means consisting of a transformer 20 couples the output of oscillator 12, supplied via winding 22, to the excitor, input, and output circuits through windings 24, 26 and 28, respectively. Winding 30 supplies feedback voltage to regulate the output of oscillator 12, which is powered by a battery 32. A second inductive coupling means consisting of isolation transformer 34 serves to couple input circuit 16 to output circuit 18.

Also shown in FIG. 1 are a monitor 36 and a body-contacting sensor 38. Monitor 36 may be any conventional electrical display or recording device meeting the requirements of the output circuit, and may be, for example, an oscilloscope or chart recorder.

Sensor 38 is a body-contacting transducer of conventional construction. In the system illustrated, sensor 38 is adapted for the measurement of blood pressure, and consists generally of two piezoresistive elements 40 and 42 (FIG. 2) mounted on a diaphragm adjacent an end of an arterial catheter. One of the two elements, which may be termed the "active" element, 40 for example, is mounted so that, with the catheter inserted in a patient's artery, blood pressure against the diaphragm causes a change in the element's resistance proportional to the pressure. Element 42, however, is mounted so that it is unaffected by blood pressure. As seen in FIG. 2, elements 40 and 42, schematically shown as variable resistances, are connected in series and form one half of a four element resistance bridge. Since both elements experience the same temperature, that of the patient's blood, element 42 serves as temperature compensation for element 40.

Referring to FIG. 2, oscillator 12 includes identical NPN transistors 46, 48, and 50. Transistors 48 and 50 comprise a conventional push-pull audio oscillator. The peak-to-peak output amplitude of the oscillator is stabilized by feedback supplied through transistor 46. The collectors of transistors 48 and 50 are connected to terminals 22a and 22b, respectively, of transformer winding 22, and are interconnected by capacitor 52, which in combination with winding 22 determines the oscillator frequency, about 2 KHz in this instance. The collector of transistor 48 is also connected through feedback capacitor 54 in series with resistor 56 to the base of transistor 50. In like manner, feedback capacitor 58 and resistor 60 connect the collector of transistor 50 with the base of transistor 48. The emitters of transistors 48 and 50 are interconnected by a conductor and connected to negative bus 62 by resistor 64, which functions to suppress spurious oscillations.

Power for the oscillator is supplied by battery 32. The negative terminal of the battery is connected to negative bus 62, and the positive terminal to terminal 68a of ON-OFF switch 68. Switch terminal 68b is connected to center tap terminal 22c of winding 22, and through load resistor 70 to the collector of feedback amplifying transistor 46.

Further describing the feedback circuitry, the collector of transistor 46 is also connected to the bases of transistors 48 and 50 through bias resistors 72 and 74, respectively, and to negative bus 62 through feedback voltage filter capacitor 76. A conductor connects the emitter of transistor 46 to negative bus 62, and the base of the transistor is connected to bus 62 through resistor 78, which shunts the current through transistor 46 into the linear portion of the conduction curve of Zener diode 80, the anode of which is connected to the base of transistor 46. The cathode of diode 80 is connected to the cathode of filter diode 82, and is connected to bus 62 through filter capacitor 84. The anode of diode 82 is connected to the cathode of filter diode 86, and through voltage doubler capacitor 88 to terminal 30a of feedback winding 30. Terminal 30b of the winding is connected to the anode of diode 86 and to negative bus 62.

In operation, the output of audio oscillator 12 is coupled into transformer 20 through output winding 22. A portion of the output, taken through feedback winding 30, is rectified by a voltage doubler circuit consisting of diodes 82 and 86, and capacitor 88, filtered by capacitor 84, referenced by Zener diode 80, amplified by transistor 46, and fed back to oscillator transistors 48 and 50 through bias resistors 72 and 74. Since the stability of this closed loop feedback circuit is determined by the impedance and temperature stability of Zener reference diode 80, this diode is chosen for minimum impedance, and maximum temperature stability, in that order. Values for capacitor 52 and winding 22 are chosen to produce the 2 KHz oscillation frequency mentioned above.

Excitor circuit 14 includes a potentiometer 90 having a resistance element 90a and a wiper 90b. Element 90a is connected in parallel across the series connected piezoresistive elements 40 and 42 of sensor 38, element 90b connecting with element 40 at junction 92, and with element 42 at junction 94. The portions of resistance element 90a between wiper 90b and junction 92, and between the wiper and junction 94 form two legs of a conventional four element resistance bridge 95, referred to hereinafter as the measuring bridge. Piezoresistive elements 40 and 42 as previously mentioned, form the other half of the bridge. Excitation for bridge 95 is taken from oscillator 12 through winding 24 on transformer 20, and applied to bridge junctions 92 and 94 through resistors 96 and 98, respectively, which compensate the temperature:strain-sensitivity characteristics of the piezoresistive elements in sensor 38. Variable resistance 100, also connected between junctions 92 and 94, sets the excitation voltage level to the bridge.

Input circuit 16 includes a conventional operational amplifier 104. A conductor connects junction 103 between resistive elements 40 and 42 with noninverting input terminal 105 of amplifier 104. The inverting input terminal 106 of the amplifier is connected to wiper 90b of potentiometer 90 through variable resistance 107, which is included to permit adjustment of amplifier gain. Inverting input terminal 106 is also connected to the ampliier output terminal 108 through feedback resistor 109. Primary winding 34a of interstage transformer 34 is connected between output terminal 108 and potentiometer wiper 90b.

Input circuit 16 also includes a powering circuit 110 for operational amplifier 104. Voltage derived from oscillator 12 via winding 26 on transformer 20 is rectified by a conventional full wave bridge rectifier circuit, connected as shown, and filtered by capacitors 112 and 114, connected between the positive and negative power supply input terminals, respectively, of amplifier 104, and the center tap terminal 26a of winding 26. Terminal 26a is also connected to potentiometer terminal 90b.

The output of amplifier 104 is coupled through transformer 34 to output circuit 18, which comprises a synchronous detector circuit 120. Detector 120 includes four diodes, connected as shown to form a bridge gate 122. A synchronizing signal taken from oscillator 12 through winding 28 on transformer 20 is applied to gate 122 through the parallel combinations of capacitor 124 and resistor 126, connected between terminal 28a of winding 28 and gate junction 128, and of capacitor 130 and resistor 132, connected between terminal 28b and gate junction 134. Capacitors 124 and 130 function to reduce signal noise in the sychronous detector by narrowing the current pulse applied to the gate diodes. Secondary winding 34b of interstage transformer 34 is connected between gate input junction 136 and common bus 138. Gate output junction 140 is connected through resistor 142 to output terminal 144. Capacitor 146, connected between junction 140 and bus 138, and capacitor 148, connected between output terminal 144 and bus 138, form, with resistor 142, a conventional R-C filter for the rectified output from detector 120. Diodes 150 and 152, connected as shown between gate junction 140 and bus 138, prevent excessively high AC voltages from being fed back to the sensor, as will be more fully explained below. Push-button switch 154, connected in series with zero-center milliammeter 156 between output terminal 144 and bus 138, is used to momentarily short the output of circuit 18 while adjusting potentiometer 90 to zero-sensor 38. Resistors 156, 158 and 160, connected in series between output terminal 144 and bus 138 serve as an output voltage divider, permitting selection of an appropriate output range for a monitor. The monitor (not shown) is connected between common terminal 162, which connects with common bus 138, and any of output terminals 144, 144a and 144b.

To summarize the operation of the circuitry described in FIG. 2, constant amplitude oscillator circuit 12 includes a conventional push-pull audio oscillator comprising transistors 48 and 50. The output from the oscillator, at a frequency of approximately 2 KHz, is coupled via transformer 20 to excitor circuit 14, input circuit 16 and output circuit 18. The output amplitude from oscillator 12 is maintained constant by a feedback circuit which includes a common-emitter amplifier comprising transistor 46. To accomplish this, a portion of the oscillator output, taken through winding 30 on transformer 20, is rectified and filtered, and, after amplification, used to control the bias on transistors 48 and 50. Oscillator circuit 12 is powered by battery 32, and as may be seen in FIGS. 1 and 2, is the only direct load on the battery. The remaining circuits, excluding the monitor, are powered indirectly by oscillator circuit 12.

As previously described, sensor 38 comprises one-half of measuring bridge 95. A portion of the oscillator output is applied to this bridge through excitor circuit 14, which includes the remaining two bridge elements. In use, sensor 38 is inserted into a blood vessel. Blood pressure on the sensor causes the resistance of active piezoresistive element 40 to change, producing an inbalance in measuring bridge 95. This inbalance causes a portion of the 2 KHz excitation voltage to appear between potentiometer wiper 90b and amplifier input terminal 105. This AC voltage, which is proportional to the blood pressure sensed by element 40, is amplified by operational amplifier 104 in input circuit 16. Power for amplifier 104 is derived by rectifying and filtering a portion of the 2 KHz output from oscillator 12, taken through winding 26 on transformer 20.

The output of this amplifier is coupled through interstage transformer 34 to a synchronous detector circuit 120. Another portion of the output of oscillator 12 taken through winding 28 on transformer 20, is applied to terminals 128 and 134 of diode gate 122. As will be understood, this AC voltage forward biases the diodes of gate 122 during a portion of the AC cycle, causing them to conduct. While thus conducting, the 2 KHz AC output of amplifier 104, appearing across secondary 34b of transformer 34 and applied to diode gate 122 at terminal 136, can pass through the gate. The output of detector 120, taken at terminal 140 of gate 122, is, therefore, a series of positive pulses. These pulses are smoothed by an R-C filter consisting of resistor 142 and capacitors 146 and 148, and the DC voltage thus obtained appears across output terminals 144 and 162. Zero-center milliammeter 156 is provided to allow measuring bridge 95 to be balanced before blood pressure measurements are taken. To do this, push-button switch 154 is momentarily closed to short the output, and wiper 90b of potentiometer 90 is adjusted to zero meter 156. Since closing switch 154 also serves to short-circuit the input of a monitor attached to output circuit 18, the monitor conveniently may be zeroed at the same time. Releasing switch 154 permits blood pressure measurements to be taken.

As previously mentioned, during patient monitoring the sensor is in direct contact with the patient's body. For the patient's safety, it is obvious that the sensor used should be isolated from sources of harmful electrical potentials.

In the system described herein, DC isolation of sensor 38 is provided by inductive coupling between the input circuit, to which the sensor is connected, and both the output circuit and the energizing circuit, permitting each of them to float electrically with respect to the others. The term "float" as used herein means that the circuits have no common DC reference level, and that the DC level of any circuit with respect to a given reference may be changed without affecting that of the other circuits. In this manner, the sensor is isolated from both the power source for the sensor signal processing apparatus, battery 32, and from monitoring device 36.

An important feature in preserving the DC isolation of sensor 38 is the construction of transformers 20 and 34. Both transformers are wound on toroidal cores which are contained in toroidal plastic insulating cases that completely surround the cores. The cores are made of a ferrite material (such as Core No. 42206-TC, J material, supplied by Magnetics, Incorporated, Butler, Pa.) with discrete windings typically of number 37 nylon insulated wire uniformly spaced around the core, neither overlapping nor wound on top of each other. Thus transformer 20 has five equally spaced winding groups, and transformer 34 has two windings on opposite sides of the core, neither winding covering more than about one-fourth of the core. This construction method eliminates both the possibility of a winding-to-winding short-circuit, and of a winding-to-core short-circuit, either of which could destroy the DC isolation of sensor 38.

The use of a ferrite core material in transformers 20 and 34 also provides an additional safety feature: minimizing the passage of power line frequency current through the system's circuits. Although the ferrite used has good magnetic coupling properties at the elevated frequency, about 2 KHz, used herein, it has poor coupling properties at normal power line frequencies, 50 and 60 Hz. Thus, a 60 Hz voltage, for example, applied to a winding of either transformer will be coupled poorly to the other windings, minimizing the passage of 60 Hz current to the sensor.

To further prevent excessively high AC voltages from being fed back to the sensor, as from a fault in a monitor attached to output circuit 18, protective diodes 150 and 152 are provided. These diodes are selected to limit the peak voltage between junction 140 of gate 122 and negative bus 138 to about 0.8 volts. Additional protection is provided by amplifier 104 which, as will be appreciated, transmits information unidirectionally, away from sensor 38.

There is thus provided an electromedical monitoring system which affords excellent protection for a patient.

Although a preferred embodiment has been described herein, it is understood that variations and modifications are possible without departing from the spirit of the invention.

It is claimed and desired to secure by Letters Patent:

1. In a system comprising a body-contacting-type electromedical sensor for providing body-condition-related information, said sensor having power input means requiring AC excitation, and an electrical monitor for displaying or recording the information, improved apparatus for transmitting said information unidirectionally between said sensor and said monitor, comprising a battery powerable oscillator,
excitor circuit means inductively coupled to said oscillator for supplying electrical AC excitation to said sensor's power input means,
an amplifier operatively connected to said sensor for receiving information therefrom and for unidirectionally transmitting such information,
powering circuit means inductively coupled to said oscillator for supplying operating power to said amplifier,
a synchronous detector inductively coupled to said amplifier for processing information received from said amplifier, and for supplying it to said monitor,
detector energizing means inductively coupled to said oscillator for energizing said detector in synchronization with the AC excitation supplied to said sensor,
first inductive coupling means inductively coupling said excitor circuit means, powering circuit means, and detector energizing means with said oscillator, and
second inductive coupling means coupling said amplifier with said synchronous detector,
said first and second inductive coupling means providing the sole electrical couplings between said oscillator, amplifier, and synchronous detector.

2. Self-contained electrical apparatus for transmitting information unidirectionally between a body-contacting electromedical sensor for providing body-condition-related information and an electrical monitor for displaying or recording the information, said sensor including power input means requiring AC excitation, and output means for providing body-condition-related information contained in an AC signal at the frequency of said excitation, said apparatus comprising powering means for said apparatus, said means comprising a battery-powerable oscillator, excitor circuit means for supplying AC excitation to such a sensor's power input means, an amplifier for receiving an information-containing signal from such a sensor and for unidirectionally transmitting a related signal containing such information, powering circuit means for supplying operating power to said amplifier, a synchronous detector for separating body-condition-related information from said related signal and for supplying the information to such a monitor, detector energizing means for energizing said detector in synchronization with the excitation supplied to such a sensor, first inductive coupling means operatively coupling said oscillator with each of said excitor circuit means, powering circuit means, and detector energizing means, and second inductive coupling means operatively coupling said amplifier with said synchronous detector.

* * * * *